(12) United States Patent
Bendiksen et al.

(10) Patent No.: US 7,931,595 B2
(45) Date of Patent: Apr. 26, 2011

(54) ULTRASOUND TRIGGERING METHOD TO REDUCE CARDIAC ARRHYTHMIA

(75) Inventors: Ragnar Bendiksen, Oslo (NO); Henrik Rasmussen, Oslo (NO); Jonny Ostensen, Oslo (NO)

(73) Assignee: GE Healthcare AS, Oslo (NO)

( * ) Notice: Subject to any disclaimer, the term of this patent is extended or adjusted under 35 U.S.C. 154(b) by 666 days.

(21) Appl. No.: 10/536,482

(22) PCT Filed: Nov. 27, 2003

(86) PCT No.: PCT/NO03/00397
§ 371 (c)(1),
(2), (4) Date: Oct. 31, 2005

(87) PCT Pub. No.: WO2004/049950
PCT Pub. Date: Jun. 17, 2004

(65) Prior Publication Data
US 2006/0155192 A1 Jul. 13, 2006

(30) Foreign Application Priority Data

Nov. 29, 2002 (NO) .................................. 20025737
Oct. 1, 2003 (NO) .................................. 20034384

(51) Int. Cl.
*A61B 8/14* (2006.01)
*A61B 8/00* (2006.01)
(52) U.S. Cl. ........................ 600/458; 600/437
(58) Field of Classification Search .................. 600/458, 600/437
See application file for complete search history.

(56) References Cited

U.S. PATENT DOCUMENTS

| | | | | |
|---|---|---|---|---|
| 5,735,281 | A | * | 4/1998 | Rafter et al. .................. 600/458 |
| 6,302,846 | B1 | * | 10/2001 | Gardner ........................ 600/458 |
| 6,306,095 | B1 | * | 10/2001 | Holley et al. ................. 600/458 |
| 6,340,348 | B1 | * | 1/2002 | Krishnan et al. ............. 600/447 |

FOREIGN PATENT DOCUMENTS

| | | |
|---|---|---|
| EP | 0619743 | 1/1997 |
| EP | 0554213 | 8/2004 |
| WO | 92/17212 | 10/1992 |
| WO | 92/17213 | 10/1992 |
| WO | 95/16467 | 6/1995 |
| WO | 0474833 | 8/1995 |
| WO | 97/29782 | 8/1997 |
| WO | 97/29783 | 8/1997 |
| WO | 98/47533 | 10/1998 |
| WO | 99/53963 | 10/1999 |

OTHER PUBLICATIONS

EA Gardner, et.al., Synchronization of contrast Agent Destruction and Imaging for Perfusion Assessment, 2000 IEEE Ultrasonics Symposium.

(Continued)

*Primary Examiner* — Tse Chen
*Assistant Examiner* — Jacqueline Cheng
(74) *Attorney, Agent, or Firm* — Robert F. Chisholm

(57) ABSTRACT

The invention relates to a triggered ultrasound imaging method for imaging of the myocardium, minimizing the risk of eliciting cardiac arrhythmia. Particularly, the invention is directed to a method of assessing cardiac perfusion. Destruction pulses are triggered such that they fall within the refractory period of the heart, while imaging pulses are triggered at any given time of the ECG cycle, preferably during end-systole.

3 Claims, 5 Drawing Sheets

OTHER PUBLICATIONS

Van der Wouw, et.al, Premature Ventricular Contractions During Triggered Imaging with Ultrasound Contrast, Journal of the American society of Echocardiography, vol. 13, No. 4, pp. 288-294.

International Search Report for PCT/NO2003/00397 dated Apr. 2004.

International Preliminary Examination Report for PCT/NO2003/00397 dated Jul. 2004.

* cited by examiner

ULTRASOUND TRIGGERING METHOD TO REDUCE CARDIAC ARRHYTHMIA

This application is a filing under 35 U.S.C. 371 of international application number PCT/N003/000397, filed Nov. 27, 2003, which claims priority to application number 20025737 filed Nov. 29, 2002 and application number 20034384 filed Oct. 1, 2003 in Norway the entire disclosure of which is hereby incorporated by reference.

FIELD OF THE INVENTION

The present invention relates to a method of triggered ultrasound imaging of the heart of a human or non-human animal subject administered with an ultrasound contrast agent wherein the risk of eliciting cardiac arrhythmia is minimized. Further the invention relates to a method of assessing perfusion of the myocardium.

DESCRIPTION OF RELATED ART

It is well known that contrast agents comprising dispersions of gas microbubbles are particularly efficient backscatterers of ultrasound by virtue of the low density and ease of compressibility of the microbubbles. For example WO 97/29783 describes such microbubble dispersions. If appropriately stabilised microbubbles may permit highly effective ultrasound visualisation of, for example, the vascular system and tissue microvasculature, often at advantageously low doses.

The following patent documents relate to ultrasound imaging involving contrast agent destruction.

It is stated in U.S. Pat. No. 5,425,366 that certain types of microparticulate ultrasound contrast agents, for example gas-containing polymer microcapsules, may be visualised by colour Doppler techniques despite being essentially motionless, e.g. as a result of uptake by the reticuloendothelial system. It is proposed that the relatively high insonication energy levels associated with colour Doppler investigations cause the microparticles to burst, thereby generating Doppler-sensitive signals described as "acoustically stimulated acoustic emission". It will be appreciated that since this technique is concerned exclusively with detection of essentially motionless contrast agent microparticles it is inherently inapplicable to measurement of rates of perfusion. Triggering techniques are not described.

WO 98/47533 is based on the finding that ultrasound imaging involving ultrasound-induced destruction or modification of contrast agents may be used to give a measure of tissue perfusion. The method described, known by various names, e.g. destruction wash-in imaging (DWI), perfusion imaging or triggered replenishment imaging (TRI), and some times called flash imaging, uses a first high-energy ultrasound pulse or series of pulses to destroy or discernibly modify a recognisable amount of the contrast agent within a target region, but rather than employing subsequent high energy pulses to detect background signals to be subtracted from the first detection sequence the method uses the subsequent low energy pulses to detect the flow of "fresh" or unmodified contrast agent (and therefore blood) into the target region. This permits determination of parameters such as vascular blood volume fraction, mean transit time and tissue perfusion with respect to local vascular state within the target region. The initial high-energy pulse or pulses may, for example, be used to clear a closely defined target region of detectable contrast agent so that a sharp front of further contrast agent, which is readily detectable and quantifiable by ultrasound imaging, then flows into this region. WO 98/47533 mentions ECG-triggering, as one of several techniques for ultrasound-induced destruction or modification of contrast agents for measurement of tissue perfusion, without any further specifications.

Ultrasound machines capable of DWI, TRI or perfusion imaging, use a first high-energy ultrasound pulse or series of such pulses, that is, destruction pulses with a high mechanical index (MI), to destroy the contrast microbubbles e.g. in the myocardium, and then demonstrate the wash-in of microbubbles in the myocardium by imaging using low energy pulses (low MI).

Generally, the ultrasound pulses used in perfusion imaging are triggered to produce discrete single pulses or a sequence of pulses for imaging or destruction of the ultrasound contrast agent in the vascular system. Technically, triggered imaging is a technique wherein the ultrasound machine is synchronized with the echocardiogram (ECG) of the heart, or similar cardiac-synchronous signal, or with a clock signal, thereby supplying a triggering signal for initiation of discrete single pulses or a sequence of pulses. When the ECG signal is used as triggering rhythm, a single or a given low number of ultrasound pulses or frame(s) is taken at the same predetermined phase of the ECG cycle, either at every heart beat (trigger interval 1:1) or at a specified interval every $n^{th}$ heart beat (trigger interval 1:n). When all ultrasound pulses triggered at every $n^{th}$ heart beat are of the same (high) energy level, usually with only single pulses, the triggering technique is called triggered interval sequencing (TIS). The imaging pulses are therefore also destruction pulses, both using the same high-energy level pulses, in TIS. TIS can be used at any given point in the ECG cycle, but is most often initiated during end-systole. Myocardial perfusion is assessed by varying the trigger interval and observing for regional differences in the trigger intervals needed before the maximum contrast "returns" in all myocardial regions. Longer trigger intervals will be needed in myocardial regions with decreased perfusion compared to regions with normal perfusion. The identical high mechanical index of destruction and imaging pulses precludes imaging of contrast build-up due to considerable microbubble destruction. As all ultrasound pulses serve as both destruction and imaging pulses, the number of high-energy triggered imaging pulses during a clinical procedure of TIS imaging is consequently high, increasing the risk of eliciting ventricular premature beats (VPBs). When the first high-energy pulse or sequence of pulses are part of a destruction imaging sequence at every $n^{th}$ heart beat, followed by low energy single pulses at every heart beat for up to n−1 heart beats, the triggering technique is called triggered replenishment imaging (TRI), as described in principle in WO 98/47533. As high-energy destruction pulse(s) are only triggered every $n^{th}$ heart beat, the number of high-energy triggered imaging pulses during a clinical procedure of TRI is consequently much lower than during a clinical procedure of TIS imaging. Irrespective of triggering technique, second harmonic or pulse inversion or some other non-linear imaging technique is usually used during triggered imaging (TIS and TRI).

The heart rhythm is divided into systole and diastole. Systole represents the period in which the ventricles contract, while diastole represents the period in which the ventricles are relaxed and dilate during filling with blood. Atrial contractions fill the heart during end-diastole. The P-wave of the ECG signal represents atrial contractions and the end of the diastole. The R-wave of the ECG signal represents initiation of ventricular contractions during start-systole. The R-wave is the amplitude that is recognized the easiest and most consistently by ultrasound machines and by adjusting the trigger delay (time of ultrasound trigger in relation to the R-wave), the actual trigger point can be adjusted throughout the length and at any point of the ECG cycle. Once the trigger delay has been adjusted to the intended value, both TIS and TRI use the same trigger delay for all triggered pulses, which is an important difference compared with the present invention. In humans, end-systolic triggered (EST) imaging uses triggering approximately at the T-wave, about 300 msec after the R-wave, and image the heart during maximal contraction. End-diastolic triggered (EDT) imaging uses triggering approximately at the P-wave. EST is most often used clinically during triggered imaging, as the heart is most contracted during this phase of the ECG cycle. More of the heart will therefore be in the imaging sector, the myocardium is thickest and the degree of shadowing in the ventricle is minimized during EST. In order to image myocardial perfusion, the contrast agent present in the myocardium has to be destroyed before the wash-in of new microbubbles can be observed. In both TIS and TRI, destruction of the gas microbubbles requires high-energy ultrasound pulses (high MI) and when high MI is used, cardiac arrhythmia, such as ventricular premature beats (VPB), may occur in relation to triggering. Trigger-induced arrhythmia occurs primarily during end-systolic triggering, which is also the most relevant time of the ECG cycle to image during contrast administration.

Generally, triggered ultrasound imaging is primarily used to minimize the ultrasound destruction of gas microbubbles and to make the visual judgement of myocardial contrast wash-in easier than during live imaging. During live imaging, the variations in base-line contrast are often higher than the contrast build-up during wash-in, hence live imaging is often little, if at all, useful for assessment of myocardial perfusion. The imaging modes, e.g. second harmonic, pulse inversion, ultra-harmonic and power modulation, used during imaging of ultrasound contrast agents take advantage of the non-linear properties of the gas microbubbles. However, as second harmonic, pulse inversion and ultra-harmonic imaging use a lower transmit frequency, they are often more destructive towards microbubbles than standard B-mode imaging at comparable mechanical index.

Some ultrasound triggering methods are described by Gardner et al. in 2000 IEEE Ultrasonics Symposium Proceedings, 1911-1915, 2000. When R-wave-triggered imaging is mentioned, actual triggering of the ultrasound pulses and imaging is not done at the R-wave of the ECG cycle, but the ultrasound machine detects the R-wave and the images are acquired at a specified time after the R-wave. All triggering in the paper is done in end-systole.

Triggered ultrasound imaging of the myocardium has been described by Van der Wouw et al. in J Am Soc. Echocardiogr. 13: 288-294, 2000 and by Van der Wouw et al. in European Heart Journal 20: 683, 1999. Van der Wouw et al. report that trigger-related ventricular premature beats (VPBs) in humans and animals are elicited during ultrasound imaging using triggered interval sequencing (TIS) technique and ultrasound contrast agent administration. Van der Wouw et al report VPBs during EST imaging (triggering at end of T-wave), while no VPBs where observed during EDT imaging (triggering at the interval from P-wave until first deflection of ECG (Q-wave)) in humans. EST is the preferred option for perfusion imaging as described above. The end-diastolic triggering method used by Van der Wouw is therefore not a suitable option for obtaining perfusion data. The present invention does not have these limitations.

There is a need for methods that permit better evaluation of coronary artery disease, and particularly measurements of tissue perfusion. Measurements of blood flow per unit of tissue mass, are of value in, for example, detection of regions of low perfusion, e.g. as a result of arterial stenosis. Measurement of cardiac perfusion in order to identify any myocardial regions supplied by stenotic arteries is of particular importance. The current invention is directed towards the use of ultrasound contrast agents, i.e. dispersions of microbubbles, in an ultrasound imaging triggering method for imaging of the myocardium, and particularly for perfusion assessments. To achieve this, it is important to define and refine ultrasound imaging triggering techniques to give methods that do not result in arrhythmia. A method of triggered ultrasound imaging of the myocardium avoiding or minimizing the risk of arrhythmia has been sought.

SUMMARY OF THE INVENTION

The following invention provides a method of triggered ultrasound imaging, for imaging of the heart wherein cardiac arrhythmia, such as VPBs, is minimized.

It has surprisingly been found that a method of triggered ultrasound imaging of the heart of a human or non-human animal subject administered with an ultrasound contrast agent, wherein one high-energy ultrasound pulse is initiated such that this pulse falls within the refractory period of the heart, is useful. According to the invention, the high-energy ultrasound pulse or a sequence of pulses with a high-energy level are hence triggered at start-systole. The low-energy imaging pulses are best triggered at end-systole.

The main advantage of the invention is that start-systolic triggering of destruction pulses according to the invention is unlikely to elicit arrhythmia, such as VPBs. Start-systolic destruction pulses do not affect the efficacy of subsequent end-systolic imaging pulses, which do not elicit VPBs due to the low energy needed.

DETAILED DESCRIPTION OF THE INVENTION

A first aspect of the invention is a method of triggered ultrasound imaging of the heart of a human or non-human animal subject administered with an ultrasound contrast agent wherein one high-energy ultrasound pulse is initiated such that this pulse falls within the refractory period of the heart.

In a preferred embodiment of the invention the high-energy ultrasound pulse is repeated to form a sequence of pulses initiated such that the first pulse of said sequence falls within the refractory period of the heart.

The method is carried out by administering a subject with an ultrasound contrast agent such that this agent is uniformly distributed in the blood pool, and subjected to ultrasound emission, e.g. from an ultrasound transducer directed at the heart, or a target region of the heart, in order to destroy or discernibly modify the circulating contrast agent. Abrupt termination of the ultrasound emission will give a substantially sharp bolus front as further contrast agent is washed in, and this may be used for assessment of the perfusion in the coronary arteries. Perfusion may be defined as a measurement of blood volume per tissue weight and unit time. The degree of regional perfusion may be assessed by monitoring the temporal development of contrast effect in different regions of tissue upon arrival of the created bolus. The arrival of contrast to tissue regions of high perfusion is expected to take place earlier than in areas of lower perfusion.

Figure 1:
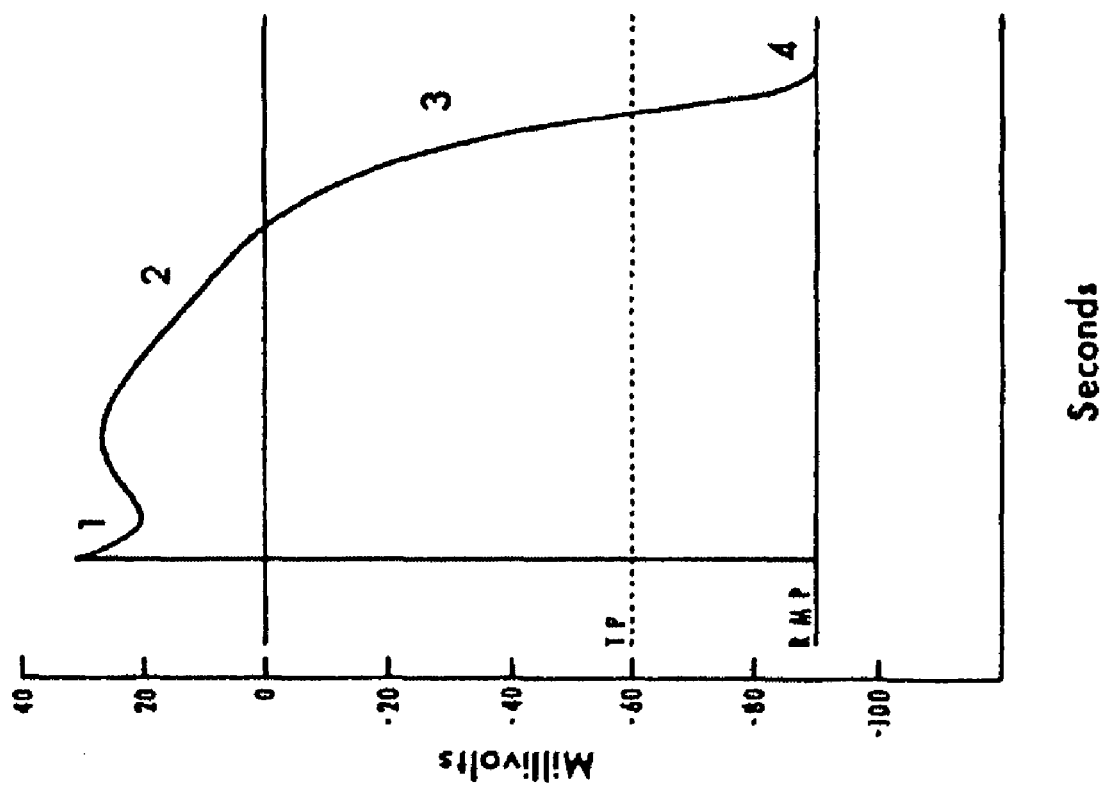
FIG. 1 illustrates the myocardial membrane action potential recording the changes in electrical potential across the membrane.

The composition of the heart can basically be divided in pacemaker cells and normal myocardial cells. The interior of myocardial cells is normally electrically negative compared to the outside environment, with a resting membrane potential (RMP) of −80 to −90 mV, that instantaneously increase to 20-30 mV during depolarisation (FIG. 1). If not excited by external (electrical) stimuli, the increase in RMP is very slow during depolarization, i.e. in practice almost stable, in normal myocardial cells, while in pacemaker cells the RMP automatically increases such that when the threshold potential (TP) of about −60 mV is reached, the cell depolarizes. Following depolarization to a membrane potential of 20-30 mV, the membrane potential decreases to the RMP in 4 phases, as shown in FIG. 1. This figure shows myocardial membrane potential measured by placing an electrode inside a muscle cell and then recording the changes in electrical potential (millivolts) that occur across the membrane over time (seconds). In phase 1, the plateau phase after depolarization, the membrane potential is more or less unchanged, while a slow decrease is initiated during phase 2. The membrane potential decreases further in phase 3, where the threshold potential (TP) is passed, before the normal RMP is regained in phase 4. During phases 1, 2 and 3, until TP is passed, the myocardial tissue is refractory to any external stimuli, while the time from TP passage (end of phase 3) and until the resting membrane potential is regained in phase 4 is relatively refractory and is excitable if stimulus is sufficiently high. Referring to the ECG-cycle shown in FIG. 2, during the normal ECG cycle, the P-wave represents the depolarization of the atria while the isoelectric period between the P-wave and the R-wave represents the delayed passage of the atrial impulses through the atrioventricular node. The ventricular depolarization is composed of 3 main phases, represented by the Q-, R- and S-wave. The Q-wave represents the first phase of ventricular depolarization (mid- and apical portions of ventricular septum) while the R-wave represents the propagation of the electrical impulse from the sub-endocardial terminations of the Purkinje fibers to the epicardial surface (free walls) of both ventricles. The S-wave represents the depolarization of the muscle fiber at the ventricular basis while the T-wave represents the ion shifting during repolarization of the myocardial cells.

Figure 2:
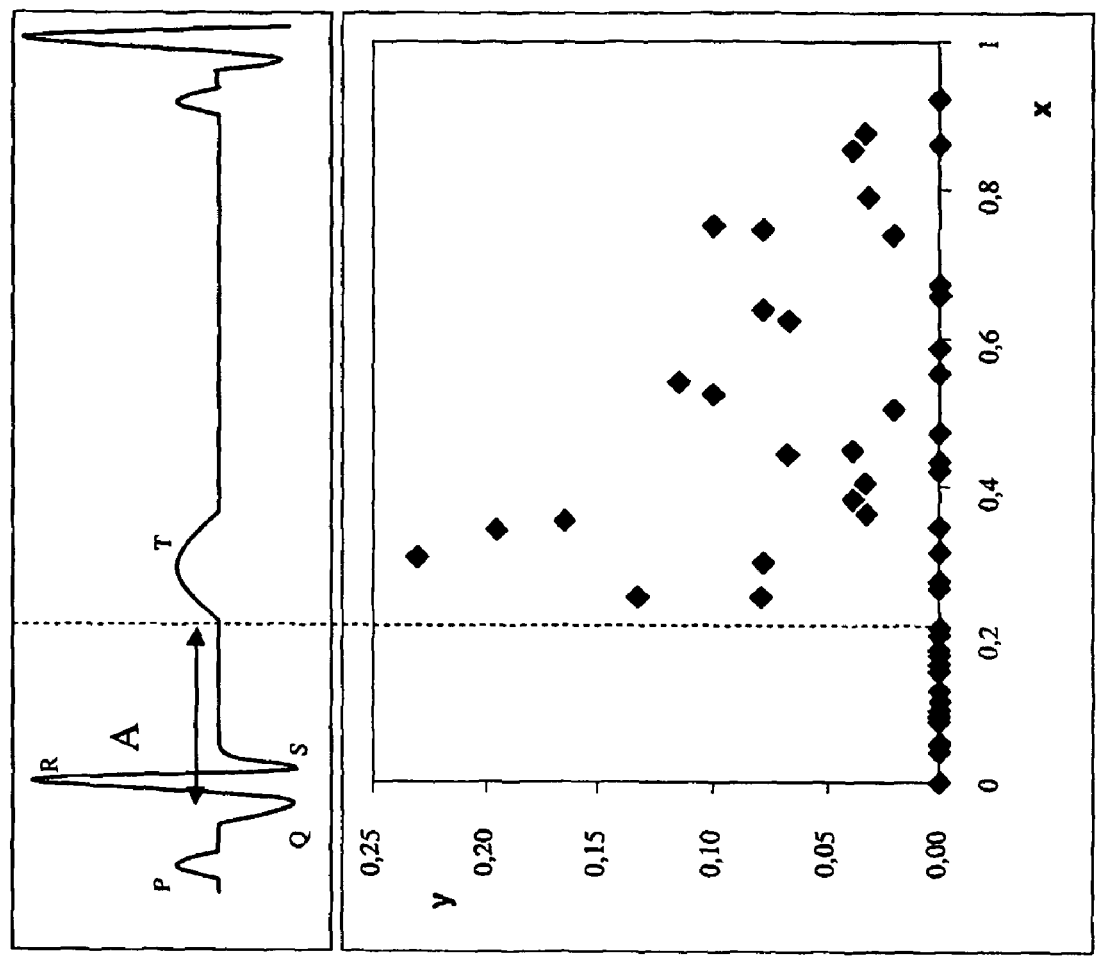
FIG. 2 illustrates the frequency of VPBs (y) as a function of relative trigger delay after the R-wave, during infusion of an ultrasound contrast agent in dogs, using Triggered Interval Sequencing (TIS) imaging, in relation to the ECG of the heart.

When the above membrane potential characteristics of single myocardial cells are applied to the heart, the ventricles are refractory to external stimuli during depolarization and the time immediately following depolarization. The Q-R-S interval and a short period thereafter, until threshold potential is regained, is therefore the refractory period of the heart. In FIG. 2 this refractory period is denoted A. We have now found that it is favourable to use an ultrasound triggering method wherein pulses with a high-energy level are initiated during this refractory period, because eliciting of any ventricular premature beats is avoided or minimized. Triggering of ultrasound high-energy pulses during start-systole (denoted A in FIG. 1) is fundamentally different from end-diastolic triggering (P-Q interval), as described by Van der Wouw et al, not only because it is a different part of the ECG cycle and because the destruction pulses used by Van der Wouw also serve as imaging pulses, but especially because the ventricles are refractory to external stimuli during start-systole, but not during end-diastole.

It has surprisingly been found that it is the time of initiation of the destruction pulse or pulse sequence, rather than the energy level, length, MI, frame-rate or pulse length of the destruction pulse sequence, which determines whether ventricular premature beats are elicited.

In a preferred embodiment of the invention a high-energy pulse or sequence of pulses are initiated at the beginning of the refractory period, i.e. in the Q-R-S interval. Further, the sequence of pulses should be continued until just before the first, second or any later end-systole after initiation, to avoid VPBs.

The high-energy pulses are applied to destruct or discernibly modify the ultrasound contrast agent. Preferably the first high-energy ultrasound pulse coincides with the R-wave of ECG of the heart and more preferably the high-energy pulse persist throughout the ECG cycle. More preferably, the sequence of high-energy pulses should be adjusted according to the heart rate such that it stops just before a T-wave of the ECG, and most preferably, it should stop just before the T-wave of the next ECG-sequence. This will minimize inflow of contrast microbubbles from end of the destruction pulses until imaging of contrast wash-in is initiated.

At the same time as the sequence of high-energy pulses stops, further low-energy imaging pulses are preferably initiated. In this embodiment low-energy pulses are preferably initiated at a T-wave. As described, triggered imaging pulses should be end-systolic (EST), but as they use an ultrasound energy level well below the lowest (ultrasound) energy level where trigger-related VPBs have been observed, no effects on cardiac rhythm are expected. The high-energy destruction pulses initiated at the R-wave are hence followed by low-energy imaging pulses initiated at a following T-wave. The imaging pulses are preferably initiated at a T-wave, but initiation at other points of the ECG may be done. The destruction pulses should then end at the same random point. Preferably the imaging pulses are initiated at the first T-wave immediately following the high-energy pulses or one heartbeat thereafter. Such imaging pulses may be triggered, as shown in FIG. 3C with triggering at every heart beat, or may be continuous as shown in FIG. 4E. In order to assess perfusion one would preferably look at a sequence of images, but a single parametric perfusion image is also a possibility.

The energy level of the initial ultrasound destruction pulses is high and the pulses should have an energy level or MI high enough to destroy or modify the contrast agent present in the imaging plane. This MI level will vary depending on the contrast agent used and the patient imaged, but typically the MI will be of at least 0.2-1.9, and preferably between 0.7-1.4. The energy level of the imaging pulses should be low and the pulses should have a mechanical index low enough to image the contrast agent without destroying it or with a minimum destruction. The MI level will again vary from agent to agent, but the level will typically be of 0.05-1.0, and preferably between 0.1-0.6.

The destruction pulses must be applied long enough to destroy or modify the contrast agent in the imaging plane and ending as close as possible to the first low-energy imaging pulse. This could be any duration, from one single ultrasound frame to several seconds. The destruction pulses will typically be sent out at the scanners regular frame rate, but since the information in these images is generally discarded the frame rate may be increased at the expense of image quality. The length of the destruction pulses may also be increased to improve the destruction of the ultrasound contrast agent.

Any ultrasound triggering method may be used, subject to that the initial destruction pulse falls within the refractory period, such as within the Q-R-S-interval, or coincides with the R-wave, of the ECG. The following imaging modes may be used; fundamental (B-mode), second (or any higher) harmonic, sub-harmonic, coherent contrast imaging, coherent pulse sequencing, pulse/phase inversion, ultra harmonic, power modulation, power pulse inversion, loss of correlation imaging and power contrast imaging and any combination of these techniques. Preferred techniques are destruction-wash-in imaging (DWI), triggered replenishment imaging (TRI) and real-time perfusion imaging (RTPI).

Myocardial triggering ultrasound techniques can be divided into three main categories, all using high-energy ultrasound pulses for gas microbubble destruction. Current use of these three techniques may all elicit trigger-related arrhythmia such as VPBs. TIS and DWI/TRI trigger according to the ECG cycle, while the third, RTPI, trigger manually. DWI and TRI are relatively identical triggering techniques. The destruction pulse sequences are of relatively high mechanical index, while the imaging pulses use low mechanical index. In known methods, both destruction pulses and imaging pulses are triggered at the same point in the ECG cycle, in the end-systole, but different trigger delays of the destruction and imaging pulses are possible. The trigger intervals of destruction pulses and the imaging pulses are variable, with a usual trigger interval of destruction pulse sequences about 1:8-1:20, while the imaging pulses are triggered at every heart beat (1:1). During DWI/TRI an initial continuous sequence of high MI destruction pulses initiated at a certain time of the ECG cycle destroys the microbubbles and the myocardial contrast. Wash-in of the gas microbubble contrast agent is then imaged at low MI by EST imaging at every heartbeat. The number of high MI EST destruction pulse sequences during a clinical procedure is consequently considerably lower with DWI/TRI compared to TIS. However, as the destruction pulse sequence of DWI/TRI in known methods is initiated during end-systole like the imaging pulses, the possibility of trigger-related arrhythmia during the first pulses of each destruction pulse sequence exist. Real-Time Perfusion imaging (RTPI) is a technique wherein a sequence of high mechanical index destruction pulses is followed by continuous imaging at low mechanical index. The operator manually initiates destruction pulses randomly at any given time during the ECG cycle. Initiation during end-systole may therefore be able to elicit trigger-related arrhythmia.

Existing ultrasound triggering techniques, and particularly the TIS technique, but also DWI/TRI and RTPI, all include the risks of inducing trigger-related ventricular premature beats (VPB) and other arrhythmia when used for cardiac imaging during infusion of gas microbubble contrast agents. Trigger-related ventricular premature beats (VPBs) in humans and animals during ultrasound imaging using the TIS technique have been reported in the literature and these findings have been confirmed in performed experiments in different animal species. FIG. 2 illustrates the probability of ventricular premature beats (y) versus trigger delay (x) during infusion of an ultrasound contrast agent (Sonazoid®), using a TIS technique and a Philips HDI 5000 US machine with a P3-2 transducer, MI 1.3, see also detailed description in Example 1. At the given time line (approximately 800 msec), a typical ECG of the heart is included in the figure, naming the different waves of the cycle. The figure shows that the probability of ventricular premature beats is highest during end-systole, around the T-wave, of the ECG. As can be seen from FIG. 2, a relative trigger delay of approximately 0.0-0.2 sec, that is the R-S interval plus time needed for repolarisation, results in no VPBs during TIS, while VPBs occur during the remaining ECG cycle (relative trigger delays of approximately 0.25-0.95 sec) and particularly during end-systole (0.25-0.35 sec).

Also, during end-systolic triggered (EST) destruction wash-in imaging (DWI) at destruction pulses of MI 1.2 with a Philips HDI 5000 ultrasound machine and a P4-2 transducer, very few, but definitely trigger-related VPBs, were observed in dogs. While some of these differences in VPB incidence between the TIS and DWI/TRI may be related to inherent differences in the nature of the ultrasound transmitted by different transducers, trigger-related VPBs are not excluded when high-energy ultrasound destruction pulses of DWI/TRI and RTPI are started during end-systole.

To avoid the induction of trigger-related VPBs during DWI/TRI and RTPI imaging during infusion of gas microbubble contrast agents, we have found that the destruction pulses and the imaging pulses should be initiated at different points of the ECG cycle. As VPBs are dependent upon myocardial gas microbubble concentration and the first pulses in the high MI destruction pulse sequences are elicited during maximal microbubble concentration, these first pulses of the destruction pulse sequence are the most likely to elicit VPBs. The chance of VPBs per pulse decreases with every pulse of the destruction pulse sequence due to continuous microbubble destruction. It has therefore been found that it is the time of initiation, rather than the length of the destruction pulse sequence, that determines whether VPBs are elicited.

Figure 3:
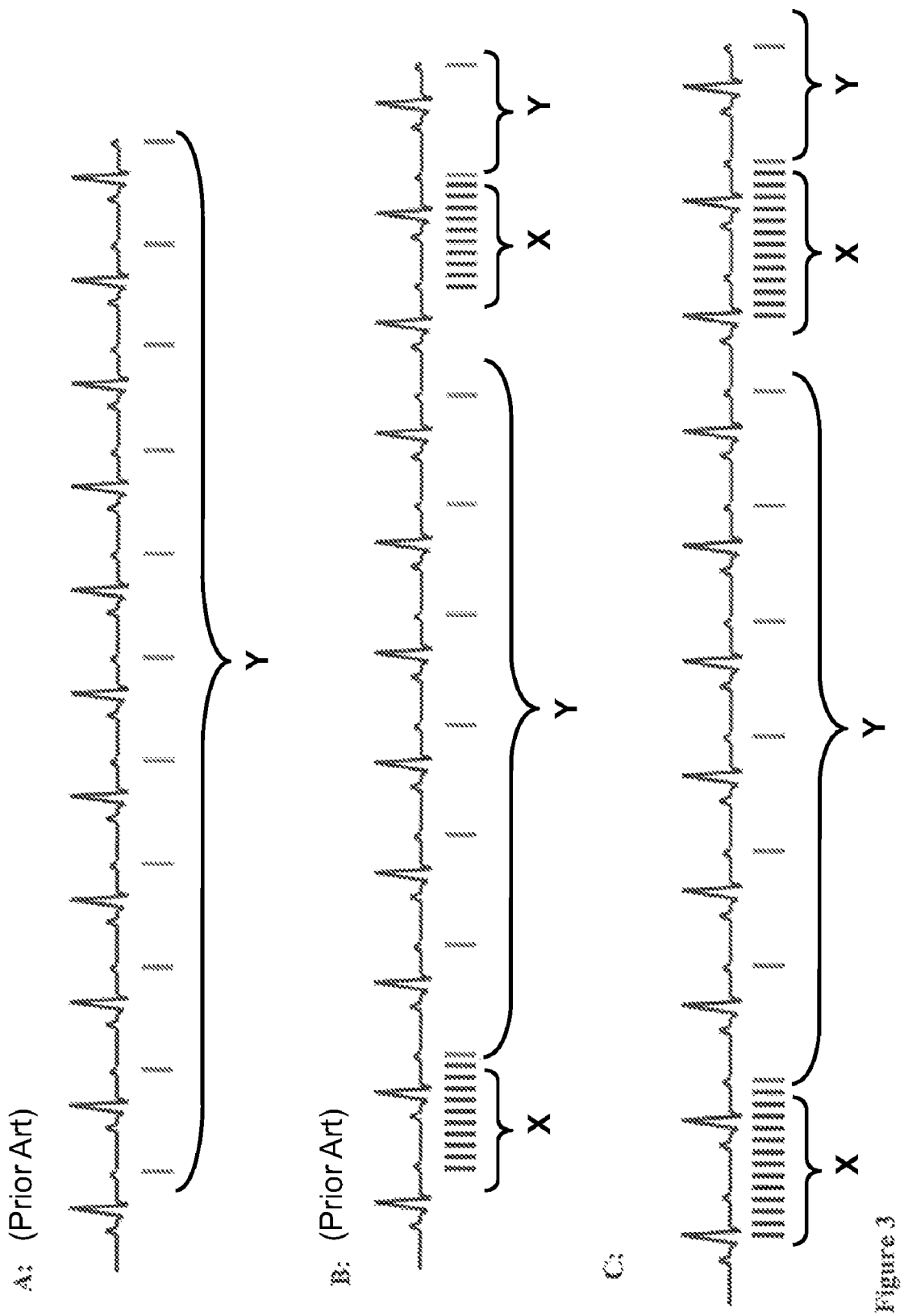
FIGS. 3 and 4 give graphical presentations of existing triggering techniques and the non-arrhythmogenic Destruction-Wash-In Imaging (DWI)/Triggered Replenishment Imaging (TRI) and Real-Time Perfusion Imaging (RTPI) techniques of the invention.
Figure 4:
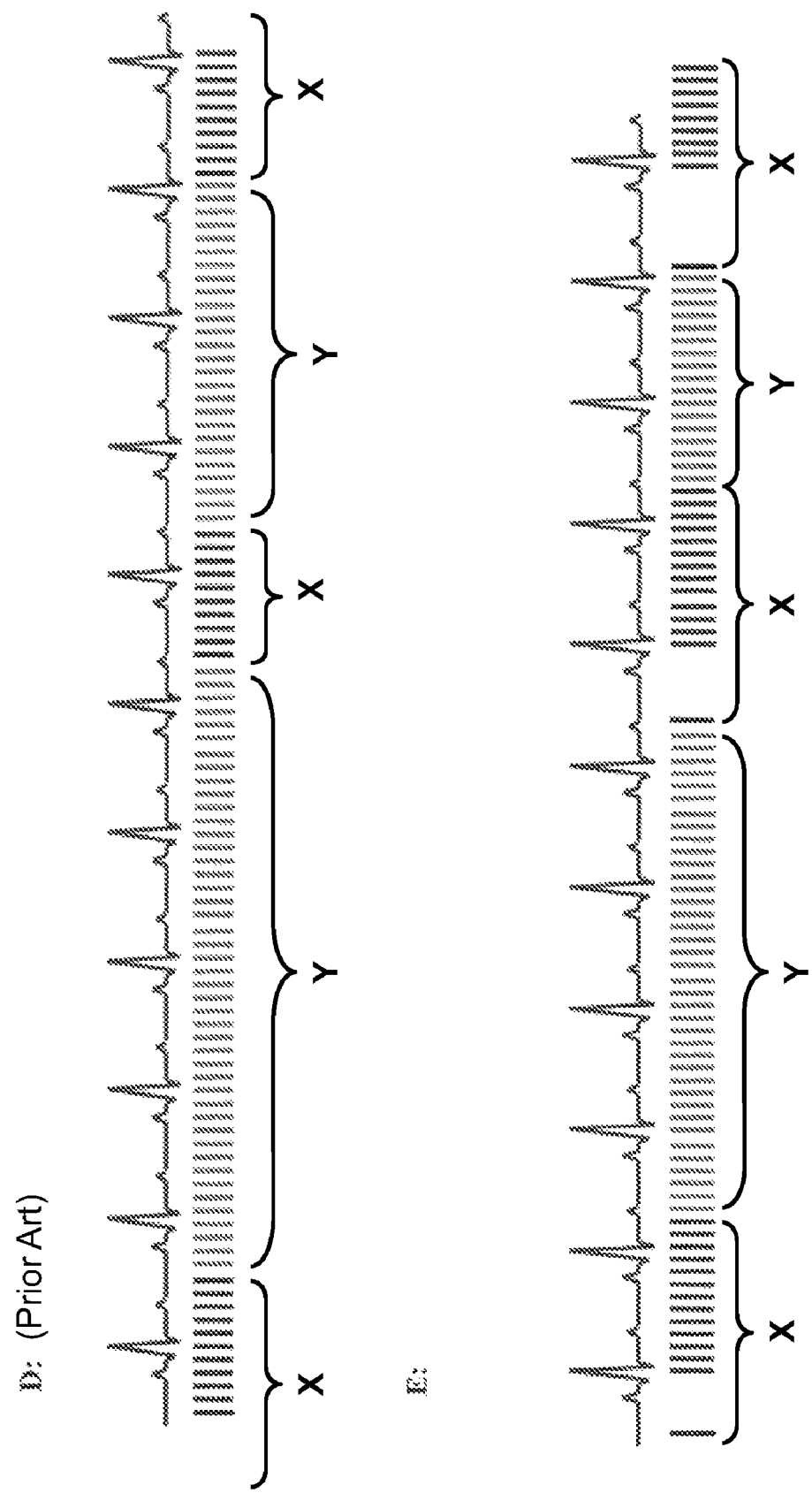

Graphical presentations of the existing techniques compared with the suggested non-arrhythmogenic triggering DWI/TRI and RTPI techniques of the invention are included in FIGS. 3 and 4. In these graphs X denotes destruction pulses and Y denotes imaging pulses. Graph A of FIG. 3 shows a standard TIS, end-systolic high MI triggering (1:1). The imaging pulses are also destruction pulses. The pulses are applied during end-systole, i.e. at the T-wave. Graph B of FIG. 3 shows a standard DWI/TRI-technique with end-systolic triggering of high MI destruction pulses (1:8) and end-systolic triggering of low MI imaging pulses (1:1). ATL HDI 5000 and Philips Sonos 5500 are examples of ultrasound machines that may be used in both examples. In both these high MI end-systolic triggered techniques there are risks of eliciting arrhythmia.

Graph C of FIG. 3 illustrates a technique of the invention. Non-arrhythmogenic DWI/TRI, R-wave triggering (i.e. start-systolic) of high-energy pulses (1:8) is followed by end-systolic triggering of the low-energy imaging pulses (1:1). This new type of non-arrhythmogenic DWI/TRI technique, triggering destruction pulses and imaging pulses at different time points in relation to the ECG, is a technical possibility today with the Philips Sonos 5500 ultrasound machine.

Graph D of FIG. 4 shows a standard real-time perfusion imaging technique (RTPI) with a random initiation of high-energy destruction pulses followed by continuous low-energy imaging. An ATL HDI 5000 may be used in such technique.

Graph E of FIG. 4 illustrates another technique of the invention. In this non-arrhythmogenic RTPI technique high-energy destruction pulses are initiated at the first R-wave, i.e. start-systolic, after an initiation decided by the operator at a random time point in the ECG cycle, and are then followed by continuous low-energy imaging. The first line in the X section indicates the initiation by the operator and not a destruction pulse.

In the techniques of the invention, shown in FIGS. 3C and 4E, the destruction pulses and the imaging pulses are initiated at different points in the EGC. The high-energy destruction pulses are initiated at the R-wave (start-systolic), while the low-energy imaging pulses are initiated at the T-wave (end-systolic). The FIGS. 3A, 3B and 4D are shown for comparison.

The preferred time delay between i.v. injection of the ultrasound contrast agent and start of data acquisition (destruction/imaging) is typically in the order of tens of seconds following a bolus injection. For an i.v. infusion of microbubbles the preferred time delay is the time required to reach an approximate steady state of contrast enhancement of the blood. A stable and consistent microbubble concentration throughout the DWI/TRI, RTPI and TIS techniques is a prerequisite for assessing microbubble wash-in as an indication of cardiac perfusion. Start of data acquisition should therefore not be started until the microbubble concentration is stable, usually 1-10 minutes after start of microbubble infusion.

In principle any free flow ultrasound contrast agent may be used in the method of the invention, subject only to the requirement that the size and stability of the contrast agent moieties are such that they are capable, following intravenous injection, of passing through the lung capillaries and generating responses in the left ventricle of the heart and the myocardial circulation. Contrast agents which comprise or are capable of generating gas microbubbles are preferred since microbubble dispersions, if appropriately stabilised, are particularly efficient backscatterers of ultrasound by virtue of the low density and ease of compressibility of the microbubbles. Ultrasound contrast agents comprising a vector having affinity for a biological target are also enclosed. The ultrasound contrast agents described by the following patent families are relevant for use in the method of the invention, for purposes of illustration and not of limitation: WO97/29783, WO92/17212, WO97/29782, EP 554213, WO-9516467, EP474833, EP 619743, U.S. Pat. No. 5,558,854, WO92/17213.

Examples of ultrasound contrast agent that may be used according to the invention are, for purposes of illustration and not of limitation, Optison®, Levovist®, Definity®, Imagent®, Sonovue®, Echogen®, Sonogen® and Sonazoid®

A variety of acquisition ways may be used to detect and quantify inflowing contrast agent following the initial ultrasound destruction, e.g. to generate a perfusion related image displaying a time-related measure of in-flowing contrast agent within the target region and thereby permitting discrimination between areas of different perfusion. The desired image may be obtained from analysis of individual scanlines or on a frame by frame basis; the former may be advantageous in areas with high rates of perfusion in order to obtain sufficient numbers of samples to discriminate areas with different perfusion, whereas the latter may be preferred in areas with low rates of perfusion.

The imaging method of the invention may be used in measurement of cardiac perfusion, and this forms a further embodiment of the invention. With the triggered ultrasound imaging method of the invention myocardial perfusion assessments, making the visual judgement of myocardial contrast wash-in easier, can be performed with no, or minimal, risk of eliciting ventricular premature heart beats. A further embodiment is hence a method of measuring or assessing myocardial perfusion in a human or non-human animal subject comprising administering an effective amount of an ultrasound contrast agent to the subject, and subjecting a target region of the myocardium with a high-energy ultrasound pulse initiated such that this pulse falls within the refractory period of the heart of the subject.

In such myocardial perfusion assessment the high-energy ultrasound pulse is preferably repeated to form a sequence of pulses initiated such that the first pulse of said sequence falls within the refractory period of the heart.

Use of an ultrasound contrast agent in a method as described is a further aspect of the invention.

Use of an ultrasound contrast agent in the manufacture of an image-enhancing composition for administration to the vascular system of a human or non-human animal subject in order to measure or assess the perfusion of the myocardium in a method wherein one high-energy ultrasound pulse is initiated such that this pulse falls within the refractory period of the heart is a further aspect. The embodiments described for the method of the invention is included in such aspect.

Preferably, the subject has been preadministered with an ultrasound contrast agent before the method of the invention is performed. In a further aspect the invention provides a method of ultrasound-induced destruction or modification of an ultrasound contrast agent preadministered to a human or non-human animal body, subjecting a target region of the heart of the body with one high-energy ultrasound pulse initiated such that this pulse falls within the refractory period of the heart, enabling destruction or modification of the contrast agent with a minimized risk of eliciting arrhythmia. Such method may further include the embodiments described for the triggered ultrasound imaging method, including repeated high-energy pulses, followed by additional low-energy pulses in order to create an ultrasound image.

The invention may be accomplished by modifying the existing software in the ultrasound machines by implementing facilities enabling automatic triggering of high mechanical destruction pulses and low mechanical imaging pulses at different time-points in relation to the ECG. The software should allow for automatic beat per beat adjustments of destruction pulse sequence length according to heart rate. The ability to trigger destruction pulses and imaging pulses at different time points in relation to the ECG is today technically possible with the Sonos 5500, but the destruction pulse sequence length is currently not automatically adjusted according to heart rate variations.

The ultrasound contrast agent could be administered as a bolus injection or by infusion, when performing the method of the invention. Preferably the contrast agent is administered by infusion. By applying high-energy pulses according to the invention, a local bolus effect is created, enabling assessment of the perfusion. Using the method in combination with bolus administration may be of interest if wanting to start destruction, in order to come back to baseline, at the R-wave without further assessment of wash-in.

While the preferred embodiment of the present invention has been shown and described, it will be obvious in the art that changes and modifications may be made without departing from the teachings of the invention. The matter set forth in the foregoing description and accompanying drawings is offered by way of illustration only and not as a limitation. The actual scope of the invention is intended to be defined in the following claims when viewed in their proper perspective based on the prior art.

EXAMPLES

In vivo studies were performed to better understand what parameters affect the occurrence of cardiac arrhythmias when performing triggered contrast echocardiography. A successful model was established, different ultrasound scanners and imaging parameters were tested and an imaging protocol for minimising the risk of trigger induced arrhythmias is suggested.

Example 1

To investigate this phenomenon, to see if a triggered imaging protocol that did not induce VPBs could be developed, Triggered Contrast Echocardiography (TCE) was conducted in mongrel dogs (Body weight: 9-32 kg, mean: 22 kg). The animals were anaesthetized with fentanyl and pentobarbital and mechanically ventilated with a respirator using room air. The protocol was approved by the local ethical committee and all procedures were terminal and performed according to current guidelines and regulations.

Three ultrasound scanners with four cardiac transducers were used. The scanners were a Philips HDI 5000 with P3-2 and P4-2 transducers (Andover, Mass., USA), a Siemens Sequoia 512 with 3V2c transducer (Mountainview, Calif., USA) and a Philips Sonos 5500 with S3 transducer (Andover, Mass., USA). Various imaging modes, MIs and triggering protocols were tested during infusion of Sonazoid™ (Amersham Health). The infusion rate was 2-5 ml Sonazoid™ per hour (2-7 times clinical dose). The dose was adjusted for maximum contrast enhancement without significant shadowing. Except for a shorter focal depth and a modified infusion procedure, all US machinery and protocols were identical to procedures used in a clinical setting.

Standard 3-lead ECG connections were placed on the extremities and the best ECG lead chosen for trigger signal and display on the US machine. All US images and associated ECG tracings were recorded continuously on videotape. Imaging was performed through the chest wall with the transducer mechanically fixated. The imaging plane was transverse mid-papillary. Each transducer was tested at max MI during second harmonic imaging (SHI), triggered in end systole-every eighth heartbeat (TIS technique). Other settings were: minimum image depth and a single focal point 4 cm deep. Ultraharmonics and Power modulation was tested in addition to SHI with the S3 transducer. With the P4-2 transducer the Triggered replenishment imaging (TRI) protocol with pulse inversion (destruction pulse MI: 0.8, 1.0 and 1.2, imaging pulse MI: 0.4) was tested in addition to SHI. With the P3-2 transducer the effect of changing the trigger delay after the R-wave of the ECG complex, the triggering interval and the MI was also studied.

The transducer settings were kept constant for 25 to 200 triggering points when acquiring VPB frequency data. The shortest observation time was used when testing the effect of variations in trigger delay, since the variation from one tested setting to the next was small (40 ms in the most sensitive area). The longest observation time was used when comparing transducers and imaging modes.

Results:

VPBs were observed in all animals after careful positioning of the transducer. The optimal imaging plane for VPB studies could not be identified by anatomical structures alone, but had to be guided by TCE with the settings most likely to elicit VPBs. When switching transducers, careful comparison with the previously videotaped imaging plane was performed to get the least possible variations in the imaging plane.

Figure 5:
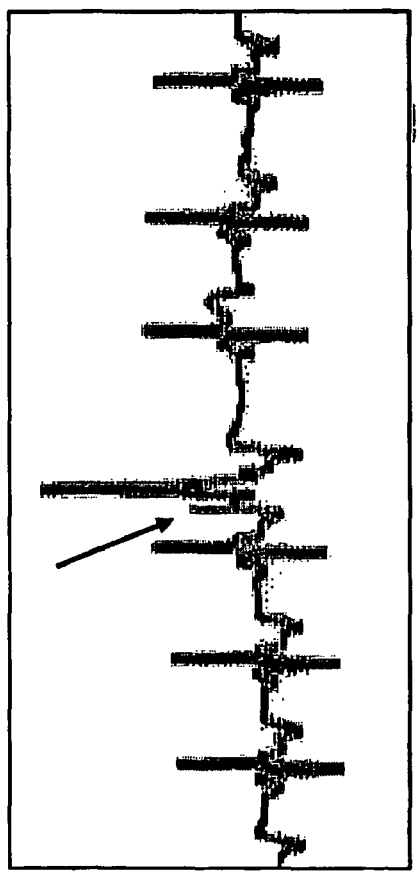
FIG. 5 shows an example of an ECG-trace captured from videotape.

FIG. 5 shows an example of an ECG-trace captured from video tape. The VPB displays an abnormal QRS complex right after the trigger point indicated by the small vertical line, marked with an arrow.

Figure 6:
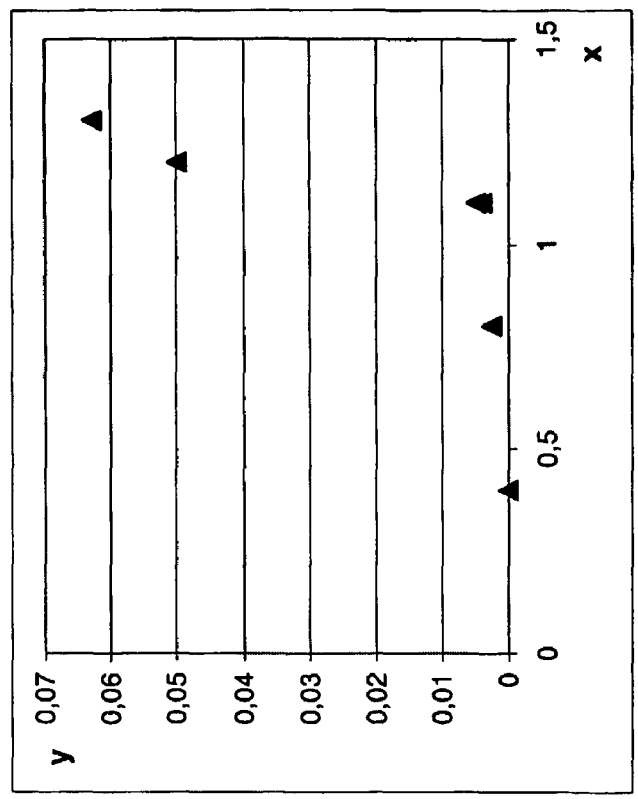
FIG. 6 gives frequency of VPBs (y) as a function of displayed MI(x) during TIS imaging of dogs administered with an ultrasound contrast agent.

FIG. 6 gives frequency of VPBs (y) as a function of displayed MI (x). 1:8 ES triggering was used with the P3-2 transducer in HPEN mode. Mean results from six animals.

FIG. 2 gives the frequency of VPBs (y) as a function of relative trigger delay after the R-wave (x). A sample ECG-trace is drawn above the graph for reference. 1:5 triggering was used to minimise the observation time when testing the effect of variations in trigger delay after the R-wave. This was tested in four animals with the P3-2 at an MI of 1.3 and a triggering interval of 1:8. The results are plotted in FIG. 2 as a function of triggering delay relative to the R-R interval (determined by the heart rate). 0 indicates the peak of the first R-wave, approximately 0.3-0.4 is end-systole and 1 is the peak of the next R-wave. There were large variations in the frequency of arrhythmias for each animal, but it was found that none of the animals had any VPBs in start-systole (A), when the heart is in a refractory phase.

No adverse events following the VPBs were observed in any of the animals.

Destruction Wash-In Imaging:

As destruction wash-in imaging is starting to be a more used method for perfusion imaging with ultrasound contrast agents, the TRI protocol with the P4-2 was tested in three animals, with TIS using the P3-2 as a positive control. The results are shown in Table 1. Only three VPBs were triggered by more than 9000 destruction pulses and 68000 imaging pulses during TRI. TIS with the P3-2 transducer gave a VPB frequency two orders of magnitude higher. All triggering was done in end-systole. See FIG. 3A for an illustration of the TIS technique and FIG. 3B for an illustration of the TRI technique. Start-systolic triggering, as given in FIG. 3C, would further have reduced the number of VPBs.

TABLE 1

| Triggering technique | Transducer | Trigger interval | MI | # of trigger events | # of VPBs | VPBs/ trigger |
|---|---|---|---|---|---|---|
| TRI destruction pulses | P4-2 | 1:8 | 0.8 | 3155 | 1 | $3.2 \cdot 10^{-4}$ |
|  |  |  | 1.0 | 3348 | 0 | 0 |
|  |  |  | 1.2 | 3335 | 2 | $6.0 \cdot 10^{-4}$ |
| TRI imaging pulses | P4-2 | 1:1 | 0.4 | 68862 | 0 | 0 |
| TIS | P3-2 | 1:8 | 1.3 | 544 | 24 | 0.044 |
|  |  |  | 1.2 | 302 | 14 | 0.046 |

What is claimed is:

1. A method of triggered ultrasound imaging of the heart of a human or non-human animal subject wherein cardiac arrhythmia is minimized, wherein the subject is administered with an ultrasound contrast agent, the method comprising the step of operating an ultrasound machine used for said imaging by initiating one high-energy ultrasound pulse or a sequence of high energy ultrasound pulses such that this one pulse or the first pulse of said sequence coincides with the R-wave of an ECG of the heart and ending this just before a T-wave of the ECG, and a further step of initiating low energy imaging pulses after the one high energy ultrasound pulse or the sequence of high energy pulses, wherein the low energy imaging pulses are initiated at or around the T-wave of an ECG of the heart where the high energy ultrasound pulse or sequence of high energy ultrasound pulses end.

2. A method as claimed in claim 1, wherein the ultrasound imaging technique used is selected from destruction-wash-in imaging, triggered replenishment imaging and real-time perfusion imaging.

3. A method as claimed in claim 1, further comprising the step of assessing myocardial perfusion.

* * * * *